United States Patent
Kim et al.

(10) Patent No.: US 11,260,066 B2
(45) Date of Patent: Mar. 1, 2022

(54) INHIBITING REDUCTION OF LEAN BODY MASS AND INHIBITING ACCUMULATION OF LIVER FAT BY ADMINISTERING ALLULOSE

(71) Applicant: SAMYANG CORPORATION, Seoul (KR)

(72) Inventors: Hye Jung Kim, Incheon (KR); Chong Jin Park, Daejeon (KR); Kang Pyo Lee, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 16/758,995

(22) PCT Filed: Oct. 27, 2017

(86) PCT No.: PCT/KR2017/012020
§ 371 (c)(1),
(2) Date: Apr. 24, 2020

(87) PCT Pub. No.: WO2019/083070
PCT Pub. Date: May 2, 2019

(65) Prior Publication Data
US 2021/0177874 A1 Jun. 17, 2021

(51) Int. Cl.
*A61K 31/7004* (2006.01)
*A23L 33/125* (2016.01)
*A23L 33/00* (2016.01)
*A61P 1/16* (2006.01)
*A61P 3/04* (2006.01)
*A61K 9/00* (2006.01)
*A61K 47/26* (2006.01)
*C12P 19/02* (2006.01)
*C12P 19/24* (2006.01)

(52) U.S. Cl.
CPC ........ *A61K 31/7004* (2013.01); *A23L 33/125* (2016.08); *A23L 33/40* (2016.08); *A61K 9/0053* (2013.01); *A61K 47/26* (2013.01); *A61P 1/16* (2018.01); *A61P 3/04* (2018.01); *C12P 19/02* (2013.01); *C12P 19/24* (2013.01); *A23V 2002/00* (2013.01)

(58) Field of Classification Search
None
See application file for complete search history.

(56) References Cited

U.S. PATENT DOCUMENTS

2018/0179604 A1* 6/2018 Kim .................. A23L 27/30
2018/0243325 A1* 8/2018 Choi ................. A61P 3/06

FOREIGN PATENT DOCUMENTS

| EP | 2754444 | 7/2014 |
|---|---|---|
| JP | 2015-182998 | 10/2015 |
| JP | 2017-119641 | 7/2017 |
| KR | 10-1318422 | 10/2013 |
| KR | 10-2014-0021974 | 2/2014 |
| KR | 10-2014-0080282 | 6/2014 |
| KR | 10-1617379 | 5/2016 |
| KR | 10-2016-0136451 | 11/2016 |
| KR | 10-1731063 | 4/2017 |
| KR | 10-2018-0026263 | 3/2018 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
KIPO, A PCT Search Report & Written Opinion of PCT/KR2017/012020 dated Jul. 26, 2018.
Kouichi Itoh et al., "Beneficial Effects of Supplementation of the Rare Sugar "D-allulose" Against Hepatic Steatosis and Severe Obesity in Lepob/Lepob Mice", Journal of Food Science, 2015, H1619-H1626. doi: 10.1111/1750-3841.12908.
Ludwig J et al., "Nonalcoholic steatohepatitis: Mayo Clinic experiences with a hitherto unnamed disease.",Mayo Clin Proc 1980, 55(7):434-438 (Abstract only); https://www.ncbi.nlm.nih.gov/pubmed/7382552.
Min-Yu Chung et al., "Hypoglycemic Health Benefits of D-Psicose", J. Agric. Food Chem., 2012, vol. 60, pp. 863-869.
Tatsuhiro Matsuo et al., "D-Psicose Is a Rare Sugar That Provides No Energy to Growing Rats", J. Nutr. Sci. Vitaminol., 2002, vol. 48, pp. 77-80.
Tatsuhiro Matsuo et al., "Metabolic effects of D-psicose in rats: studies on faecal and urinary excretion and caecal fermentation", Asia Pacific J Clin Nutr 2003;12 (2): 225-231.
Roy L. et al., "D-Psicose metabolism in the rat*", Carbohydrate Research, 34 (1974) 200-202.
S.H. Baek et al., "D-Psicose, a Sweet Monosaccharide, Ameliorate Hyperglycemia, and Dyslipidemia in C57BL/6J db/db Mice", Journal of Food Science 75(2): H49-53, 2010.
Tatsuhiro Matsuo et al.,"Dietary D-psicose, a C-3 epimer of D-fructose, suppresses the activity of hepatic lipogenic enzymes in rats", Asia Pacific J Clin Nutr 10(3): 233-237.
Tatsuhiro Matsuo et al., "Less Body Fat Accumulation with D-Psicose Diet versus D-Fructose Diet", J Clin. Biochem. Nutr., 30, 55-65, 2001.
Tatsuhiro Matsuo et al., "Effects of Supplemental D-Psicose on Glucose Tolerance and Serum Adipocytokine Levels in Rats Fed a High-Fat Diet or a Low-Fat Diet", J. Oleo Sci., 53(9), 453-460 (2004).
Young-Mee Chung et al., "Dietary D-Psicose Reduced Visceral Fat Mass in High-Fat Diet-Induced Obese Rats", Journal of Food Science 77(2): H53-8, 2012.

(Continued)

*Primary Examiner* — Dale R Miller
(74) *Attorney, Agent, or Firm* — Lex IP Meister, PLLC (57) ABSTRACT

The present invention relates to a composition for inhibiting liver fat accumulation comprising allulose as an active ingredient and a pharmaceutical composition and a food composition using thereof.

7 Claims, 1 Drawing Sheet

(56) References Cited

OTHER PUBLICATIONS

Takako Yamada et al., "Effects of D-psicose on Body Fat Accumulation and High Fructose Corn Syrup Diets in Rats", NSKKK. vol. 57, No. 6, 263-267 (2010).
Tetsuo Iida et al., "Acute D-Psicose Administration Decreases the Glycemic Responses to an Oral Maltodextrin Tolerance Test in Normal Adults", J Nutr Sci Vitaminol, 54, 511-514, 2008.
Noriko Hayashi et al., "Study on Postprandial Blood Glucose Suppression Effect of D-Psicose in Borderline Diabetes and the Safety of Long-Term Ingestion by Normal Human Subjects", Biosci Biotechnol Biochem., 74(3) 510-519, 2010.
Tatsuhiro Matsuo et al., "Effects of Dietary D-Psicose on Diurnal Variation in Plasma Glucose and Insulin Concentrations of Rats", Biosci Biotechnol Biochem., 70(9) 2081-2085, 2006.
Tatsuhiro Matsuo et al., "D-Psicose Inhibits Intestinal Alpha-Glucosidase and Suppresses the Glycemic Response after Ingestion of Carbohydrates in Rats", J Clin Biochem Nutr., 45, 202-206, 2009.
Mohammad A Hossain et al., "Rare sugar D-psicose improves insulin sensitivity and glucose tolerance in type 2 diabetes Otsuka Long-Evans Tokushima Fatty (OLETF) rats", Biochem Biophys Res Commun 405 (2011) 7-12.
Akram Hossain et al., "Rare sugar D-psicose protects pancreas b-islets and thus improves insulin resistance in OLETF rats", Biochem Biophys Res Commun. 425 (2012) 717-723.
Youngji Han et al, "D-Allulose supplementation normalized the body weight and fat-pad mass in diet-induced obese mice via the regulation of lipid metabolism under isocaloric fed condition", Molecular Nutrition & Food Research, DE, (Feb. 27, 2016), vol. 60, No. 7, pp. 1695-1706, XP055600971.
Yasuo Nagata et al, "D-Psicose, an Epimer of D-Fructose, Favorably Alters Lipid Metabolism in Sprague-Dawley Rats", Journal of Agricultural and Food Chemistry, US, (Jan. 1, 2015), vol. 63, No. 12, pp. 3168-3176, XP055517512.
EPO, European Search Report of EP 17929787.4 dated May 17, 2021.
Masaru Ochiai et al., "D-Psicose increases energy expenditure and decreases body fat accumulation in rats fed a high-sucrose diet", Int J Food Sci Nutr, Oct. 21, 2013.
Ryuichi Hasegawa et al., "Proposal of new uncertainty factor application to derive tolerable daily intake", Regulatory Toxicology and Pharmacology, 58 (2010), 237-242, Jun. 16, 2010.

* cited by examiner

INHIBITING REDUCTION OF LEAN BODY MASS AND INHIBITING ACCUMULATION OF LIVER FAT BY ADMINISTERING ALLULOSE

TECHNICAL FIELD

The present invention relates to a pharmaceutical composition and a food composition for prevention or improvement of nonalcoholic fatty liver disease comprising allulose as an active ingredient, and more specifically, a composition for inducing prevention or improvement of nonalcoholic fatty liver disease by inhibiting liver fat accumulation with allulose administration.

BACKGROUND ART

Fatty liver disease, also called fatty liver, is a disease which causes liver failure due to abnormal accumulation of fat (such as triglycerides) in liver cells. It is known that the initial condition of fatty liver disease is simple fatty liver that recognizes only fat deposition in liver cells, and then it progresses to steatohepatitis (including hepatic fibrosis), and also cirrhosis or hepatocellular carcinoma. In general, causes of fat deposition in the liver include alcohol intake, obesity, diabetes, lipid metabolism abnormalities, drugs (steroids, tetracyclines, etc.), Cushing syndrome, poisoning (yellow phosphorus, etc.), high nutritional disorders, and the like.

The causes of fatty liver disease are largely divided into alcoholic and nonalcoholic, and the liver disease caused by the former is called alcoholic fatty liver disease (also called alcoholic liver failure), and the liver disease caused by the latter is called nonalcoholic fatty liver disease (NAFLD, or nonalcoholic steatohepatitis).

Nonalcoholic fatty liver disease means simple fatty liver which is not accompanied by an inflammatory response in patients who do not consume excess alcohol, and a wide range of diseases including nonalcoholic steatohepatitis (NASH) showing hepatocellular inflammation advanced thereby, liver fibrosis and cirrhosis, and is a broad concept compared to non-alcoholic steatohepatitis (Ludwig J et al., Mayo Clin Proc 1980, 55(7):434-438) used in the past.

Nonalcoholic fatty liver disease refers to fatty change (steatosis) and lobular hepatitis (steatohepatitis), and the like, which are characteristic features of alcoholic hepatitis in liver biopsy despite the absence of a history of alcohol intake that is deemed harmful to the liver. The pathology of the liver shows various spectrums from simple fatty liver (Nonalcoholic Fatty Liver, NAFL) to steatohepatitis (Nonalcoholic Steatohepatitis, NASH), fibrosis accompanied with steatohepatitis, cirrhosis, and the like, and the nonalcoholic fatty liver disease is used as a meaning including all of these.

There are no established treatments for such nonalcoholic fatty liver, because it is associated with various factors such as diabetes, obesity, coronary artery disease, sedentary habits, and the like. Obesity is an important target in treatment of nonalcoholic fatty liver disease, because a factor associated with insulin resistance which is a risk factor for liver damage, the amount of fatty acids entering the liver, and reduction of inflammatory or fibrotic adipokine can be induced by weight loss. The alanine aminotransferase (ALT) level and triglyceride content in the liver can be reduced by dietary control and weight loss by exercise, but the improvement by weight loss is little known in patients with necrotic inflammation or liver fibrosis.

As described above, there are not established methods for sufficient treatment of nonalcoholic fatty liver disease. It is important to prevent or avoid nonalcoholic fatty liver disease in advance.

DISCLOSURE

Technical Problem

An embodiment of the present invention provides a pharmaceutical composition or a food composition for prevention or improvement of nonalcoholic fatty liver disease comprising allulose as an active ingredient.

An embodiment of the present invention provides a method for prevention or improvement of nonalcoholic fatty liver disease comprising administering allulose to a subject in need.

Another embodiment of the present invention provides a pharmaceutical composition or a food composition for alleviation, prevention, improvement or inhibition of nonalcoholic fatty liver disease by inhibition of liver fat accumulation, comprising allulose as an active ingredient.

An embodiment of the present invention provides a method for alleviation, prevention, improvement or inhibition of nonalcoholic fatty liver disease by inhibition of liver fat accumulation, comprising administering allulose to a subject in need.

Technical Solution

The present invention relates to a composition, for example, a pharmaceutical composition or a food composition, for inhibition of liver fat accumulation, and prevention or improvement of nonalcoholic fatty liver disease, comprising allulose as an active ingredient.

In addition, the present invention relates to a method for prevention or improvement of nonalcoholic fatty liver disease comprising administering allulose to a subject in need. The subject may be a mammal including animals and humans. The subject may be a patient with nonalcoholic fatty liver disease.

The composition comprising allulose as an active ingredient according to the present invention inhibits liver fat accumulation and inhibits reduction of muscle tissue, thereby functioning to improve the composition of body.

Nonalcoholic fatty liver disease means simple fatty liver which is not accompanied by an inflammatory response in patients who do not take alcohol excessively, and diseases with wide concept including nonalcoholic steatohepatitis (NASH) showing hepatocellular inflammation processed from the simple fatty liver, liver fibrosis and cirrhosis, and is a broad concept compared to non-alcoholic steatohepatitis used in the past (Ludwig J et al., Mayo Clin Proc 1980, 55(7):434-438).

Nonalcoholic fatty liver disease refers to diseases showing fatty change (steatosis) and lobular hepatitis (steatohepatitis), and the like, which are characteristic features of alcoholic hepatitis in liver biopsy, despite no history of alcohol intake as considered to be harmful to the liver. The pathology of the liver shows various spectrums from simple fatty liver (Nonalcoholic Fatty Liver, NAFL) to steatohepatitis (Nonalcoholic Steatohepatitis, NASH), fibrosis accompanied with steatohepatitis, cirrhosis, and the like, and the nonalcoholic fatty liver disease, and the nNonalcoholic fatty liver disease is referred to include all of them.

For the composition including allulose as an active ingredient according to the present invention, the change of body fat weight measured by DXA at 12 weeks showed a statistically significant difference between three groups compared to the baseline. Lean body mass is the measuring amount of water, muscle protein, bone, etc. with excluding the fat amount from the body weight, and can explain whether the body weight loss is caused by a change in body compositions other than body fat or a change in body fat. For the composition comprising allulose as an active ingredient according to the present invention, the lean body mass measured by DXA at 12 weeks did not show a significant difference in the low-dose group and high-dose group in 12-week analysis compared to the baseline, but it showed a significant difference in the control group with reduced value at 12 weeks compared to the baseline. It could be confirmed that the body weight loss was caused by the body fat change, as the reduction of body fat mass was statistically significant. It is possible to achieve a very desirable health result, because it is effective in inhibition of body fat accumulation, but is not accompanied by changes or is very small changes in other beneficial body components (water, muscle, bone, etc.).

The allulose may be an agent which inhibits reduction of lean body mass statistically significantly. In the inhibition of reduction of lean body mass, the average change of the lean body mass measured before/after administration may be 1.5% or less, preferably 1.0% or less at 12 weeks compared to the baseline.

In the liver CT, the control group showed a tendency to decrease in all Liver HU mean value, Liver–Spleen HU, and Liver/Spleen HU, and showed a statistically significant difference before and after administration. In the test of present invention, blood liver enzyme indicators reflecting liver function showed commonly improved results after taking allulose. The nonalcoholic fatty liver disease is considered as other phenotype of metabolic syndrome caused by obesity. In conclusion, according to the results of analyzing the human body components, allulose inhibited body fat accumulation and muscle mass reduction.

In addition, in in vitro test, the alkaline phosphatase and γ-GTP showed a statistically significant difference between three groups, as they are reduced in the high-dose group and low-dose group and were increased in the control group at 12 weeks compared to the baseline. The ALT showed a statistically significant difference between three groups, as it was reduced in the high-dose group and low-dose group but was increased in the control group, and it showed a statistically significant difference before/after administration in the high-dose group. The nonalcoholic steatohepatitis is other phenotype of metabolic syndrome caused by obesity.

The content of allulose in the composition of an embodiment of the present invention may be for example, 0.01 to 100% by weight based on the total weight of the composition, but not particularly limited thereto.

The subject that the composition of the present invention is administered to may be a subject in need of inhibiting liver fat accumulation, and may be an animal including normal human or patient. In addition, it may be a human having need of inhibiting liver fat accumulation, nonalcoholic fatty liver diseases, a risk of the diseases, or a cause of the diseases such as obesity, overweight, and etc.

Herein, the term "administration" means behavior of introducing the composition of the present invention to a subject by certain proper method, and an administration route can be administered through various oral or parenteral routes, preferably oral administration, as long as it can reach target tissue.

The administration frequency of the composition of the present invention may be one to four times in a day or may be several times by dividing the daily dose, but not particularly limited thereto. For example, when allulose is administered 1-4 times in a day, it may be administered by spitting the dose into equal amounts or different amounts.

The daily dose of the allulose may be 0.05 to 0.75 g, or preferably 0.05 to 0.75 g per unit weight kg of a subject, and may be 3 to 45 g, preferably 3 to 25 g, or more preferably, 6 to 12 g, for a human having average body weight of 60 kg.

The allulose in the composition of the present invention may be a powder or syrup form, or for example, the allulose may be powder with a purity of 90% by weight or more, or a solution prepared at various concentrations using the powder, or a solution obtained by converting a fructose-containing solution to allulose by a chemical or biological method.

In addition, the allulose may be used alone, or may be mixed saccharide including additional other saccharides, and the example of the mixed saccharide may contain 1 to 99.9 parts by weight of allulose based on 100 parts by weight of the total solid content of the mixed saccharide, and may further comprise one or more kinds selected from the group consisting of fructose, glucose and oligosaccharide.

A specific example of the mixed saccharide containing allulose may comprise 2 to 55 parts by weight of allulose, 30 to 80 parts by weight of fructose, 2 to 60 parts by weight of glucose and 0 to 15 parts by weight of oligosaccharide, based on 100 parts by weight of the total solid content of the mixed saccharide, and it may not include oligosaccharide. All of allulose, fructose and glucose are preferably D-isomers.

The allulose may be prepared by chemical synthesis or a biological method using allulose epimerase, and preferably, it may be prepared by a biological method. Accordingly, the allulose may be prepared by reacting fructose-containing raw materials with a composition for producing allulose comprising one or more kinds selected from the group consisting of allulose epimerase, cells of microorganism producing the epimerase, culture of the microorganism, lysate of the microorganism, and extract of the lysate or fermentation product. In an embodiment of the present invention, as the method for preparing allulose according to a biological method, it may be produced by using microorganism or recombinant microorganism producing allulose epimerase or in which a gene encoding allulose epimerase is introduced, and reacting the allulose epimerase obtained therefrom with fructose-containing raw materials. The allulose epimerase may be used in a liquid phase reaction or solid phase reaction using immobilized enzyme.

In order to perform the efficient production of allulose in the method for producing allulose, the concentration of fructose used as a substrate may be 20 w/w % or more, for example, 40 to 98% (w/v), or 40 to 95% (w/v), or particularly, 40 to 75% or 50 to 95% (w/v), based on the total reactants. The concentration of fructose may be appropriately selected in consideration of the economic feasibility of the process and the solubility of fructose. The fructose may be used as a solution dissolved in a buffer solution or water (for example, distilled water).

The detailed description of the allulose and its preparation method are described in Korean Patent Publication No. 2014-0021974, Korean Patent Publication No. 2014-0080282, and Korean Patent No. 10-1318422.

The food composition of the present invention may be prepared in various forms by common methods known in the art, and the allulose may be provided by being prepared as a kind of food, beverages, food additives, beverage additives, health functional food, and the like. For example, it may be beverages such as tea, juice, carbonated drinks, ion drinks, and drinks; health food preparations such as powder, tablets, and capsules; food such as gum, snack, bread and noodle, and the like. In the food composition of the present invention, a sweetener, a flavor, a flavoring agent, and the like may be comprised in addition to the active ingredient. In addition, the food composition of the present invention may comprise a preservative, an emulsifier, a thickener, and the like, if needed. The food composition of the present invention may be prepared and processed in a form of tablets, capsules, powder, granules, liquid, pills and the like, for the purpose of preventing or improving nonalcoholic fatty liver disease.

Herein, "health functional food" refers to food prepared (including processing) using a raw material or component having useful functionality to a human body according to Law for Health Functional Foods, and "functionality" means obtaining a useful effect for health uses such as maintaining normal functions of a human body or maintaining and improving health through activation of physiological functions. In addition, the functionality means a nutrient function that is a physiological action of nutrients for growth and enhancement and normal functions of a human body; a physiological function that is an action of contribution or improvement for health, or maintenance and improvement of health by having a special effect on normal functions or biological activity of a human body; or a function of reducing disease occurrence and risk by food intake.

The food is not particularly limited as long as it is an allulose applicable food, and for example, it may be processed grains, processed beans, processed potatoes, processed sugar, processed fish products, other processed products, confectionery, candy (e.g., hard candy, jelly, gummi), bread, dumpling, processed meat, processed egg, jellied food, processed oil, other noodles, fried noodles, solid tea, liquid tea, coffee, fruit juice, fruit beverage, other fermented beverage, ginseng red ginseng beverage, mixed beverage, beverage base, seasoned miso, red pepper paste, fermented soybean paste, sauces, complex seasoned food, cabbage kimchi, seasoned salted fish, pickles, sugar pickles, boiled agricultural products, boiled livestock products, seasoned dried fish, dried fish, peanut or nut processed products, fruit processed products, seasoned seaweed, extracted food, ready-to-eat food, steamed rice, mushroom fruit body processed food beverage, meat processed products, chocolate, confectionery, pizza, noodles (ramen, noodles, etc.), gums, ice cream, alcoholic beverage, vitamin complexes, and health supplements, and the like.

The food according to the present invention may comprise general food additives, and the suitability of food additives is determined by standards and criteria for corresponding items in accordance with the general rules and general test methods of Food Additives Code approved by the Korea Food and Drug Administration, unless otherwise specified.

The items described in the "Food Additives Code" include for example, chemical compounds such as ketones, glycine, calcium citrate, nicotinic acid, cinnamomic acid, etc.; natural additives such as chromic pigment, licorice extract, crystalline cellulose, Kaoliang pigment, guar gum, etc.; and mixed preparations such as an L-sodium glutamate preparation, an alkaline agent for noodles, a preservative preparation and a tar colorant, etc., and the like. The composition for prevention or improvement of nonalcoholic fatty liver according to the present invention may be used as a pharmaceutical composition or a food composition.

In an embodiment of the present invention, the pharmaceutical composition for prevention or improvement of nonalcoholic fatty liver may be prepared as a pharmaceutical composition. The pharmaceutical composition according to the present invention may be orally or parenterally administered, and preferably, it is administered orally.

The pharmaceutical composition according to the present invention comprises a pharmaceutically acceptable carrier. The carrier is commonly used for formulation, and includes lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil and the like, but not limited thereto. The pharmaceutical composition according to the present invention may further comprise a lubricant, moisturizer, sweetener, flavor, emulsifier, suspending agent, preservative, or the like. For reference, pharmaceutically acceptable carriers and preparations are described specifically in Remington's Pharmaceutical Sciences (19th ed., 1995).

An appropriate dose of the pharmaceutical composition according to the present invention may be variously prescribed by considering the factors such as formulation method, administration method, patient's age, body weight, gender and the disease condition, food, administration time, administration route, excretion rate, and response sensitivity.

The pharmaceutical composition of the present invention may be formulated by formulating with a pharmaceutically acceptable carrier and/or excipient, inn a unit dose form or a multi-dose container.

Advantageous Effects

The present invention relates to a pharmaceutical composition and a food composition for prevention or improvement of nonalcoholic fatty liver disease comprising allulose as an active ingredient, and more specifically, relates to a composition for inducing prevention or improvement of nonalcoholic fatty liver disease by administering allulose and thereby inhibiting liver fat accumulation.

MODE FOR INVENTION

Figure 1:
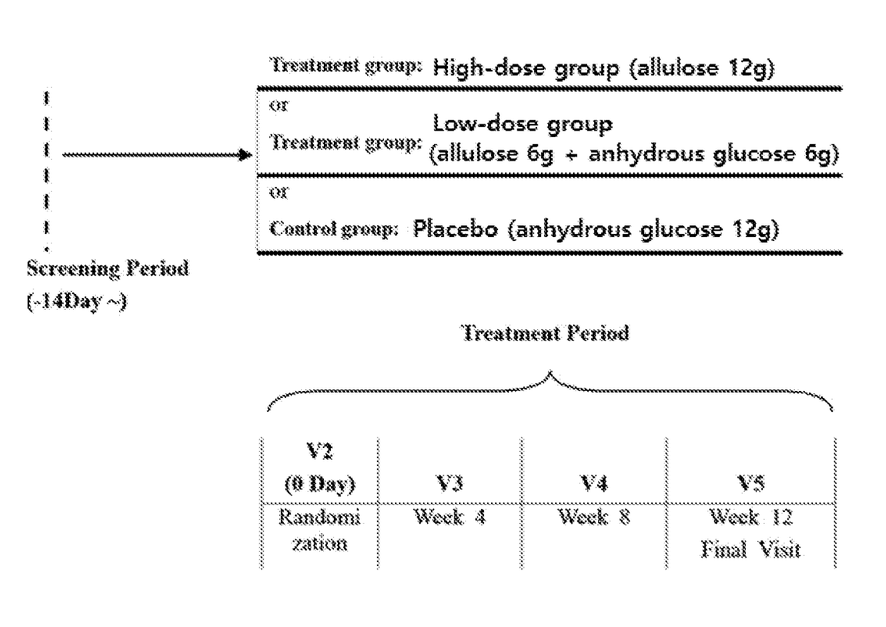
FIG. 1 is a schematic diagram showing the human application method according to An embodiment of the present invention.

Hereinafter, the present invention will be described in more detail by the following examples. However, these examples are intended to illustrate the present invention only, but the scope of the present invention is not limited by these examples.

Preparative Example 1. Preparation of Allulose

The allulose powder used in the following example was prepared by the method described in Korean Patent Publication No. 2014-0021974, Korean Patent Publication No. 2014-0080282 and Korean Granted Patent No. 10-1318422.

Example 1: Efficacy Test

(1) Subject Selection

After conducting a screening test for those who heard the detailed description of the purpose and research method of the present example and agreed in writing as subjects, those who met the selection/exclusion criteria were selected. The specific selection criteria are as follows, and the final selected subjects are 99 men and women who are overweight or obese, and the demographic information of the selected subjects is shown in the following Table 1.

Selection Criteria

1. Adult men and women between ages of full 19 to 75
2. Overweight adult men and women with BMI of 23 kg/m2 or more to less than 30 kg/m2
3. In case of women of childbearing age, negative in pregnancy test during screening
4. Patients that can be controlled (diabetes or hypertension, etc.): patients that are well controlled with drugs are included, and 10% of the subjects have hypertension and 5% have diabetes.

The gender of the subject participating in the present human application test were 5 men (15.15%) and 28 women (84.85%) in the high-dose group, 6 men (18.18%) and 27 women (81.82%) in the low-dose group, and 2 men (6.06%) and 31 women (93.94%) in the control group. The average age was 45.06 years old (range: 25-65 years old) in the high-dose group, 41.52 years old (range: 26-61 years old), and 44.61 years old (range: 26-63 years old) in the control group, and both gender and age did not show a statistically significant difference in the subject distribution.

By dividing 99 selected subjects into 3 groups, the test subjects were finally determined as the high-dose group (33 people), low-dose group (33 people) and control group (33 people).

TABLE 1

|  | High-dose group | Low-dose group | Control | p-value |
|---|---|---|---|---|
| ITT | 33 | 33 | 33 |  |
| Age |  |  |  |  |
| Mean | 45.06 | 41.52 | 44.61 | 0.3698 |
| SD | 12.06 | 10.31 | 11.00 |  |
| Median | 42.00 | 40.00 | 46.00 |  |
| Min | 25.00 | 26.00 | 26.00 |  |
| Max | 65.00 | 61.00 | 63.00 |  |
| Gender |  |  |  |  |
| Male | 5 (15.15) | 6(18.18) | 2 (6.06) | 0.4184[1] |
| Female | 28 (84.85) | 27(81.82) | 31(93.94) |  | p-value: Kruscal-wallis test
[1]Fisher's exact test

(2) Test Products

The efficacy test was performed by dividing 99 selected test subjects into 3 groups, and by providing three products to the high-dose group (33 people), low-dose group (33 people), and control group (33 people), respectively. The allulose high-dose product was provided to the high-dose test group, and the allulose low-dose product was provided to the low-dose test group, and placebo product was provided to the control group.

The products were stored in airtight containers, at a room temperature (1-30° C.), in a dry and well-ventilated place.

TABLE 2

| Product name | allulose high-dose | allulose low-dose | placebo |
|---|---|---|---|
| component name | allulose | allulose, anhydrous glucose | anhydrous glucose |
| type and formulation | white crystalline powder | white crystalline powder | white crystalline powder |
| amount of raw material product | allulose 12 g/d | allulose 6 g/d, anhydrous glucose 6 g/d | anhydrous glucose 12 g/d |
| packaging unit | 6 g/bag | 6 g/bag | 6 g/bag |

(3) Intake Method

Ninety nine (99) subjects were randomly assigned to the high-dose group, low-dose group or control group, with including 33 subjects in each test group. In three test groups, the products were mixed in 100 ml of water and were administered orally twice a day.

As the daily dose for one test subject, 12 g allulose in the high-dose group, 6 g allulose and 6 g anhydrous glucose in the low-dose group, and 12 g anhydrous glucose in the control group were divided and provided twice a day. It was administered from the day after the random assignment day (0 day), and was taken with drinking water twice at morning and evening with meals for 12 weeks.

At the random assignment day (0 day), the efficacy evaluation items and safety evaluation items such as DXA measurement and the like were checked, and the evaluation items were also checked through hospital outpatient visit at 4 weeks, 8 weeks and 12 weeks from the day of beginning administration of test products. In addition, during the human application test, the usual physical activity of subjects was investigated using Korean version of International Physical Activity Questionnaire (IPAQ). During the human application test period, the subjects were trained to maintain the activity amount being similar to normal physical activity. At each hospital outpatient visit, the amount of meal intake was examined by the recording board made by the subjects. The subjects were trained to maintain the amount of meal intake being similar to the usual amount with avoiding overeating condition.

Example 2: Efficacy Evaluation Method

(1) Body Fat and Lean Body Mass Measured by DXA

At the time of second hospital visit (visit 2) and final hospital visit (visit 5), the body fat ratio and body fat were measured using prodigy DXA of U.S. Lunar Company.

For the body fat measured by DXA, after calculating the change of the body fat after 12 weeks compared to the base time, technical statistics (mean, standard deviation, median value, minimum value, maximum value) were obtained. The comparative statistic test for the three groups was performed using ANOVA or Kruscal-Wallis test by testing whether data were normally distributed. When there was a significant difference between the three groups, the multiple comparison was conducted through Tukey-Kramer method. In order to find out whether there was a difference in the mean change in a group, it was analyzed using Paired t-test or Wilcoxon's signed rank test.

(2) Glucose Index Test

At the time of screening hospital visit (visit1), visit2 and final visit (visit5), FBS, Insulin, and HbA1c test was conducted for the collected blood.

After calculating the average change of the glucose index (FBS, Insulin, HbA1c) after 12 weeks compared to the base time, technical statistics (mean, standard deviation, median value, minimum value, maximum value) were obtained. The comparative statistic test for the three groups was performed using ANOVA or Kruscal-Wallis test by testing whether data were normally distributed. When there was a significant difference between the three groups, the multiple comparisons were conducted through Tukey-Kramer method. In order to find out whether there was a difference in the mean change in a group, it was analyzed using Paired t-test or Wilcoxon's signed rank test.

(3) Liver CT

In order to evaluate the degree of fat deposition in the liver at the time of hospital visit 2 and visit 5, the HU of liver, HU of spleen, HU difference of liver and spleen (Liver minus Spleen), and HU ratio of liver and spleen (Ratio Between Liver and Spleen) after 12 weeks compared to the base time were measured. CT attenuation values (Hounsfield units) were measured in regions of interest (ROI) selected as a homogeneous place avoiding blood vessels in the right lobe of liver and spleen in one non-contrast-enhanced abdominal CT image including both liver and spleen three times, and the average value was taken as each CT attenuation number. Then, the size of each region of interest was designated equally as 120 mm$^2$.

Through liver CT, for HU of liver, HU of spleen, HU difference of liver and spleen (Liver minus Spleen), and HU ratio of liver and spleen (Ratio Between Liver and Spleen) after 12 weeks, technical statistics (mean, standard deviation, median value, minimum value, maximum value) were proposed for the average change compared to the base time. The comparative statistic test for the three groups was performed using ANOVA or Kruscal-Wallis test by testing whether data were normally distributed. When there was a significant difference between the three groups, the multiple comparisons were conducted through Tukey-Kramer method. In order to find out whether there was a difference in the mean change in a group, it was analyzed using Paired t-test or Wilcoxon's signed rank test.

(4) Blood chemical test result The test items performed at screening visit (visit1), visit2 and end visit (visit5) were Alkaline phosphatase, AST, ALT, and γ-GTP.

In case of continuous data, for the average change compared to the base time, technical statistics (mean, standard deviation, median value, minimum value, maximum value) were proposed for the average change compared to the base time. The comparative statistic test for the three groups was performed using ANOVA or Kruscal-Wallis test by testing whether data were normally distributed. When there was a significant difference between the three groups, the multiple comparison was conducted through Tukey-Kramer method. In order to find out whether there was a difference in the mean change in a group, it was analyzed using Paired t-test or Wilcoxon's signed rank test. In case of categorical data, technical statistics (frequency, percentage) were proposed, and comparative statistic test was performed between three groups using Chi-square test or Fisher' exact test.

Example 3: Efficacy Evaluation Result (1) Body Fat and Lean Body Mass Measured by DXA For 99 8ITT analysis subjects, the average change in bod fat at 12 weeks compared to the base time was increased by 0.25±1.34 kg in the high-dose group and was increased by 0.16±0.91 kg in the low-dose group, and was increased by 0.95±1.65 kg in the control group, and it showed a statistically significant difference between three groups (p-value=0.0358). In addition, the control group showed a statistically significant difference before and after at 12 weeks compared to the base time (p-value=<0.0001).

The average change of the lean item did not show a statistically significant difference between three groups, and in the control group, the average change at 12 weeks compared to the base time was reduced by −0.61±1.28 kg, and thereby showed a statistically significant difference (p-value=0.0048). The result of body fat measured by DXA was shown in the following Table 3.

TABLE 3

|  |  | High-dose group | Low-dose group | Control | p-value[a] |
|---|---|---|---|---|---|
| ITT |  | 33 | 33 | 33 |  |
| Fat (Kg) | Mean | 26.06 | 26.64 | 26.18 | 0.8735 |
| Baseline | SD | 4.36 | 4.74 | 5.28 |  |
| 12 W | Mean | 26.31 | 26.80 | 27.13 | 0.7920 |
|  | SD | 4.59 | 4.76 | 5.41 |  |
|  | Difference | 0.25 ± 1.34 | 0.16 ± 0.91 | 0.95 ± 1.65 | 0.0358[1]+ |
|  | p-value[b] | 0.2937 | 0.3177 | <0.0001[2] |  |
| Lean(Kg) | Mean | 40.46 | 42.21 | 39.74 | 0.7691[1] |
| Baseline | SD | 6.94 | 9.12 | 6.64 |  |
| 12 W | Mean | 40.24 | 42.26 | 39.13 | 0.4607[1] |
|  | SD | 6.75 | 9.40 | 6.63 |  |
|  | Difference | −0.22 ± 1.08 | 0.05 ± 0.89 | −0.61 ± 1.28 | 0.0884[1] |
|  | p-value[b] | 0.2522 | 0.7373 | 0.0048[2] |  | p-value[a]: ANOVA
p-value[b]: Paired t-test
[1]Kruskal-wallis test
[2]Wilcoxon's signed rank test
+P-value < 0.05, statistically significant, post hoc method by tukey low-dose group versus control group For the body fat item measured by DXA, the variance at 12 weeks compared to the base time showed a statistically significant difference between three groups. In the control group, the increase of the body fat showed a statistically significant difference before and after administration. However, the allulose low-dose group and high-dose group were slightly increased, but there was no statistically significant difference before and after administration.

The lean body mass was reduced by −0.61±1.28 kg after 12 weeks in the control group, but the allulose administration groups did not show a difference before and after administration. As overweight was included in selection criteria of subjects in this study, all subjects were in mild obesity group (average body mass index is 27 or less), and it is considered that there was no statistically significant change in weight or body mass index due to the lack of subjects per group. The reduction of muscle mass was suppressed.

(2) Glucose Index

As the result of the glucose index test for 99 ITT analysis subjects, the difference of the average change at 12 weeks compared to the base time between the high-dose group, low-dose group and control group was not significant for all the items of Glucose, Insulin, and HbAlc, and there was no statistically significant difference between the groups before and after, so there was no hypoglycemic effect in the analysis subjects as normal blood sugar. The result of glucose index analysis of analysis subjects was shown in the following Table 4, Table 5 and Table 6.

TABLE 4

|  |  | High-dose group | Low-dose group | Control | p-value[a] |
|---|---|---|---|---|---|
| ITT |  | 33 | 33 | 33 |  |
| Glucose(mg/dl) | Mean | 94.70 | 94.76 | 93.85 | 0.8542 |
| Baseline | SD | 9.72 | 10.16 | 12.21 |  |
|  | Median | 93.00 | 94.00 | 92.00 |  |
|  | Min | 76.00 | 78.00 | 80.00 |  |
|  | Max | 122.00 | 128.00 | 145.00 |  |
| 12 W | Mean | 94.58 | 97.18 | 92.64 | 0.4407 |
|  | SD | 10.62 | 13.72 | 11.93 |  |
|  | Median | 94.00 | 97.00 | 91.00 |  |
|  | Min | 78.00 | 79.00 | 66.00 |  |
|  | Max | 126.00 | 140.00 | 139.00 |  |
|  | Difference | −0.12 ± 8.35 | 2.42 ± 10.10 | −1.21 ± 8.36 | 0.3770 |
|  | p-value[b] | 0.9341[2] | 0.2410 | 0.4110[2] |  | p-value[a]: Kruskal-wallis test
p-value[b]: Wilcoxon's signed rank test
1) ANOVA
[2]Paired t-test

TABLE 5

|  |  | High-dose group | Low-dose group | Control | p-value[a] |
|---|---|---|---|---|---|
| ITT |  | 33 | 33 | 33 |  |
| Insulin (mg/dl) | Mean | 6.95 | 7.92 | 6.75 | 0.4110 |
| Baseline | SD | 3.01 | 5.84 | 3.77 |  |
|  | Median | 6.20 | 6.50 | 5.30 |  |
|  | Min | 3.10 | 2.40 | 2.00 |  |
|  | Max | 18.20 | 36.20 | 20.00 |  |
| 12 W | Mean | 8.70 | 9.18 | 6.65 | 0.1273 |
|  | SD | 5.34 | 9.94 | 3.14 |  |
|  | Median | 7.50 | 7.10 | 5.80 |  |
|  | Min | 2.10 | 2.30 | 2.40 |  |
|  | Max | 31.20 | 61.30 | 13.80 |  |
|  | Difference | 1.75 ± 5.33 | 1.27 ± 5.15 | −0.10 ± 2.60 | 0.4399 |
|  | p-value[b] | 0.0629 | 0.0814 | 0.4801 |  | p-value[a]: Kruskal-wallis test
p-value[b]: Wilcoxon's signed rank test
1) ANOVA
2) Paired t-test

TABLE 6

|  |  | High-dose group | Low-dose group | Control | p-value[a] |
|---|---|---|---|---|---|
| ITT |  | 33 | 33 | 33 |  |
| HbA1 (mg/dl) | Mean | 5.61 | 5.57 | 5.52 | 0.4325 |
| Baseline | SD | 0.36 | 0.44 | 0.43 |  |
|  | Median | 5.60 | 5.50 | 5.40 |  |
|  | Min | 5.00 | 4.80 | 5.00 |  |
|  | Max | 6.60 | 7.20 | 6.90 |  |
| 12 W | Mean | 5.66 | 5.64 | 5.56 | 0.4527 |
|  | SD | 0.35 | 0.49 | 0.43 |  |

TABLE 6-continued

|  | High-dose group | Low-dose group | Control | p-value[a] |
|---|---|---|---|---|
| Median | 5.60 | 5.60 | 5.50 | |
| Min | 5.00 | 4.90 | 5.00 | |
| Max | 6.50 | 7.20 | 6.90 | |
| Difference | 0.05 ± 0.18 | 0.07 ± 0.22 | 0.04 ± 0.14 | 0.8846[1] |
| p-value[b] | 0.1159 | 0.0915 | 0.0996[2] | | p-value[a]: Kruskal-wallis test
p-value[b]: Wilcoxon's signed rank test
[1] ANOVA
[2] Paired t-test (3) Liver CT As the result of the CT test tested for 99 ITT analysis subjects, the average change at 12 weeks compared to the base time did not show a statistically significant difference between three groups in all the items. All the Liver HU average value, Liver–Spleen HU, and Liver/Spleen HU items showed a decreasing tendency in the liver CT, and showed a statistically significant difference before and after (p-value=0.0300, 0.0027, 0.0029).

TABLE 7

|  |  | High-dose group | Low-dose group | Control | p-value[a] |
|---|---|---|---|---|---|
| ITT Liver CT |  | 33 | 33 | 33 | |
| Liver HU Mean(HU) | | | | | |
| Base line | Mean(HU) | 58.27 | 55.86 | 59.62 | 0.9676 |
|  | SD | 10.30 | 14.86 | 7.12 | |
| 12 W | Mean | 57.49 | 55.17 | 57.77 | 0.6497 |
|  | SD | 11.21 | 15.36 | 7.57 | |
|  | Difference | −0.78 ± 5.60 | −0.69 ± 5.17 | −1.85 ± 4.68 | 0.3310 |
|  | p-value[b] | 0.4304[2] | 0.5903 | 0.0300[2] | |
| Spleen HU Mean(HU) | | | | | |
| Base line | N | 33 | 32 § | 33 | |
|  | Mean | 49.80 | 51.07 | 49.86 | 0.2269[1] |
|  | SD | 3.40 | 2.65 | 3.81 | |
| 12 W | Mean | 50.30 | 50.66 | 50.76 | 0.8207[1] |
|  | SD | 3.16 | 3.06 | 3.10 | |
|  | Difference | 0.50 ± 2.77 | −0.41 ± 2.34 | 0.90 ± 3.37 | 0.0676 |
|  | p-value[b] | 0.3069[2] | 0.1549 | 0.1354[2] | |
| Liver - Spleen HU+ | | | | | |
| Base line | N | 33 | 32 § | 33 | |
|  | Mean | 8.47 | 5.30 | 9.76 | 07957 |
|  | SD | 9.72 | 14.86 | 7.87 | |
| 12 W | Mean | 7.19 | 4.75 | 7.01 | 0.8278 |
|  | SD | 10.94 | 15.15 | 8.04 | |
|  | Difference | −1.28 ± 5.36 | −0.55 ± 5.43 | −2.75 ± 4.85 | 0.2277 |
|  | p-value[b] | 0.1802[2] | 0.5726[2] | 0.0027[2] | |
| Liver/Spleen (HU) ++ | | | | | |
| Base line | N | 33 | 32 § | 33 | |
|  | Mean | 1.17 | 1.11 | 1.20 | 0.6829 |
|  | SD | 0.20 | 0.30 | 0.17 | |
| 12 W | Mean | 1.14 | 1.09 | 1.14 | 0.8544 |
|  | SD | 0.23 | 0.31 | 0.16 | |
|  | Difference | −0.03 ± 0.11 | −0.01 ± 0.11 | −0.06 ± 0.11 | 0.1204 |
|  | p-value[b] | 0.1903[2] | 0.8942 | 0.0029[2] | |

+ Difference of Liver and Spleen (Liver minus Spleen)
++ Ratio of Liver and Spleen (Ratio between Liver and Spleen)
§ R012 subject was excluded from the test, because the spleen scan was not measured at the base time.
p-value[a]: Kruskal-wallis test
p-value[b]: Wilcoxon's signed rank test
[1] ANOVA
[2] Paired t-test (4) Blood Chemical Test Result The difference of the average change at 12 weeks compared to the base time by each blood chemical test items between the groups was analyzed, and Alkaline phosphatase (p-value=<0.0001), ALT (SGPT) (p-value=0.0127), and γ-GTP (p-value=0.0043) in the blood chemical test items showed a statistically significant difference between three groups.

The Alkaline phosphatase and γ-GTP showed a statistically significant difference in the three groups, as they were reduced in the high-dose group and low-dose group and a statistically significant difference before/after administration in the high-dose group and low-dose group, and they were increased in the control group. ALT showed a statistically significant difference between three groups, as it was reduced in the high-dose group and low-dose group and was increased in the control group, and a statistically significant difference before/after administration in the high-dose group.

TABLE 8

| | | High-dose group | Low-dose group | Control | p-value |
|---|---|---|---|---|---|
| ITT | | 33 | 33 | 33 | |
| Blood chemical test | | | | | |
| Alkaline phosphatase(U/L) | Mean | 183.21 | 178.97 | 175.03 | 0.9119[1)] |
| | SD | 56.52 | 49.53 | 41.85 | |
| | Median | 169.00 | 170.00 | 165.00 | |
| | Min | 104.00 | 102.00 | 112.00 | |
| | Max | 331.00 | 328.00 | 270.00 | |
| AST(SGOT)(U/L) | Mean | 18.76 | 22.64 | 19.24 | 0.5445[1)] |
| | SD | 5.33 | 10.52 | 6.66 | |
| | Median | 18.00 | 18.00 | 17.00 | |
| | Min | 10.00 | 12.00 | 10.00 | |
| | Max | 28.00 | 53.00 | 41.00 | |
| ALT(SGPT)(U/L) | Mean | 22.21 | 26.88 | 20.39 | 0.4768[1)] |
| | SD | 13.90 | 18.82 | 13.41 | |
| | Median | 16.00 | 19.00 | 17.00 | |
| | Min | 7.00 | 10.00 | 8.00 | |
| | Max | 61.00 | 76.00 | 68.00 | |
| γ-GTP (U/L) | Mean | 18.18 | 33.58 | 24.12 | 0.0640[1)] |
| | SD | 12.64 | 47.95 | 19.56 | |
| | Median | 14.00 | 19.00 | 16.00 | |
| | Min | 7.00 | 8.00 | 7.00 | |
| | Max | 61.00 | 270.00 | 81.00 | | p-value: ANOVA
[1)]Kruskal-wallis test
*p-value < 0.05, statistically significant The Alkaline phosphatase and γ-GTP items showed a statistically significant difference between three groups, as they were reduced in the high-dose group and low-dose group and they were increased in the control group, and a statistically significant difference before/after was shown in the high-dose group and low-dose group. ALT showed a statistically significant difference between three groups as it was reduced in the high-dose group and low-dose group and it was increased in the control group, and a statistically significant difference before/after was shown in the high-dose group. In this test, blood liver enzyme indexes reflecting liver function commonly showed the improved result after taking allulose, and nonalcoholic fatty liver disease is considered as another phenotype of metabolic syndrome caused by obesity. In conclusion, the results of analyzing the above body components showed that allulose inhibited body fat accumulation and muscle mass reduction.

Example 4: Safety Test

In the physiochemical test for the safety, the low-dose group and high-dose group were examined as normal or clinically insignificant abnormal opinion in all items, and there was no statistically significant difference between the three groups. Twelve (12) specific items of the physiochemical test (ITT, Ears/Nose/Throat, Eye, /Head/Neck, Cardiovascular system, Abdomen, Respiratory system, Breast/Genitalia, Neurological system, Lymph nodes, Skin, Musculoskeletal, etc.) were classified into three (3) categories of "Normal, Abnormal (Not Clinically Significant), and Abnormal (Clinically Significant)", and they were examined as normal or Abnormal (Not Clinically Significant) opinion in all the items, and there was no statistically significant difference between three groups.

In addition, in the test result of vital signs, the average change in systolic blood pressure was reduced by 4.15±10.30 mmHg in the high-dose group and was reduced by 2.67±9.71 mmHg in the low-dose group, and was increased by 1.73±9.63 mmHg in the control group, at 8 weeks compared to the base time, which showed a statistically significant difference between the three groups (p-value=0.0349). The diastolic blood pressure and pulse rate did not showed statistically significant difference between three groups.

Furthermore, the difference of the average change between the three groups at 12 weeks compared to the base time for the items was analyzed in the laboratory test. In the blood chemical test items, Alkaline phosphatase (p-value=<0.0001), ALT (SGPT) (p-value=0.0127), and γ-GTP (p-value=0.0043) showed statistically significant difference between the three groups. As the result of comparing the normality of the urine test, there was no clinically significant abnormal subject, and all items did not showed statistically significant difference between three groups.

The invention claimed is:

1. A method for inhibiting reduction of lean body mass and inhibiting accumulation of liver fat comprising administering, to an overweight subject having a BMI of 23 kg/m$^2$ or more to less than 30 kg/m$^2$, a daily dose of allulose at 0.05 to 0.75 g per kg of the subject, wherein the average change of the lean body mass measured before and after administration is 1.5% or less at 12 weeks.

2. The method according to claim 1, wherein the daily dose of the allulose is administered at an amount of 3 to 45 g to the subject.

3. The method according to claim 2, wherein the daily dose of the allulose is administered at an amount of 3 to 25g to the subject.

4. The method according to claim 2, wherein the daily dose of the allulose is administered at an amount of 6 to 12g to the subject.

5. The method of claim 1, wherein the daily dose of the allulose is administered by splitting the dose 1 to 4 times.

6. The composition according to claim 1, wherein the administration is oral administration.

7. The composition according to claim 1, wherein the allulose is a component in a mixed saccharide syrup, or in a powder obtained from a mixed saccharide syrup, that comprises 2 to 55 parts by weight of allulose, 30 to 80 parts by weight of fructose, 2 to 60 parts by weight of glucose and 0 to 15 parts by weight of an oligosaccharide, based on the total solid content of the mixed saccharides.

* * * * *